(12) United States Patent
Karlsson et al.

(10) Patent No.: US 11,137,407 B2
(45) Date of Patent: Oct. 5, 2021

(54) METHOD OF DIAGNOSING ARTHRITIS OR OTHER JOINT DEGRADING DISEASE

(71) Applicant: LYNXON AB, Gothenburg (SE)

(72) Inventors: Niclas Karlsson, Gothenburg (SE); Chunsheng Jin, Gothenburg (SE); Sebastian Kalamajski, Lund (SE); Sarah Ann Flowers, Arlington, VA (US)

(73) Assignee: Lynxon AB, Gothenburg (SE)

( * ) Notice: Subject to any disclaimer, the term of this patent is extended or adjusted under 35 U.S.C. 154(b) by 0 days.

(21) Appl. No.: 16/078,818

(22) PCT Filed: Feb. 23, 2017

(86) PCT No.: PCT/EP2017/054117
§ 371 (c)(1),
(2) Date: Aug. 22, 2018

(87) PCT Pub. No.: WO2017/144563
PCT Pub. Date: Aug. 31, 2017

(65) Prior Publication Data
US 2019/0094243 A1    Mar. 28, 2019

(30) Foreign Application Priority Data
Feb. 23, 2016 (SE) .................................. 1650230-4

(51) Int. Cl.
*G01N 33/53* (2006.01)
*G01N 33/68* (2006.01)

(52) U.S. Cl.
CPC ..... *G01N 33/6887* (2013.01); *G01N 33/5308* (2013.01); *G01N 33/6893* (2013.01); *G01N 2333/78* (2013.01); *G01N 2440/36* (2013.01); *G01N 2440/38* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 6,596,476 B1 * | 7/2003 | Lesniewski .......... | C07K 14/005 435/5 |
| 2002/0009761 A1 | 1/2002 | Hutchins et al. | |
| 2007/0111327 A1 | 5/2007 | Jay | |
| 2020/0141939 A1 * | 5/2020 | Bang .................... | G01N 21/75 |

FOREIGN PATENT DOCUMENTS

WO    0064930 A2    11/2000

OTHER PUBLICATIONS

Harlow, E. and Lane, D., Antibodies: A Laboratory Manual (1988) Cold Spring Harbor Laboratory Press, Cold Spring Harbor, NY, pp. 23-26 (Year: 1988).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
International Search Report and Written Opinion dated May 17, 2018, for corresponding International Application No. PCT/EP2017/054117; International Filing Date: Feb. 23, 2017 consisting of 10-pages.
Ritter et al, "Mass Spectrometry Assays of Plasma Biomarkers to Predict Radiographic Progression of Knee Osteoarthritis", Arthritis Research & Therapy 2014, vol. 16, No. 5.
Lord et al, "Current Serological Possibilities for the Diagnosis of Arthritis with Special Focus on Proteins and Proteoglycans from the Extracellular Matrix", Expert Rev Mol Diagn 2015.
Ai et al, "Anti-lubricin Mono-clonal Antibodies Created using Lubricin-knockout Mice Immunodetect Lubricin in Several Species and in Patients with Healthy and Diseased Joints", PLOS ONE, vol. 10, No. 2, 2015.
Svala E et al, "Characterisation of Lubricin in Synovial Fluid from Horses with Osteoarthritis", Equine Veterinary Journal, 2015.
Coles J M et al, "Molecular Mechanisms of Aqueous Boundary Lubrication by Mucinous Glycoproteins", Current Opinion in Colloid & Interface Science, 2010.
C Jin et al, "Human Synovial Lubricin Expresses Sialyl Lewis x Determinant and Has L-selectin Ligand Activity", Journal of biological chemistry, vol. 287, No. 43, 2012.

* cited by examiner

*Primary Examiner* — Gary Counts
(74) *Attorney, Agent, or Firm* — Christopher & Weisberg, P.A.

(57) ABSTRACT

The invention provides a method of diagnosing arthritis or other joint degrading disease in a subject which comprises determining whether there is a presence or increase of lubricin having a joint tissue posttranslational modification, in a blood sample from the subject, the presence or increase of the lubricin having the joint tissue posttranslational modification indicating arthritis or other joint degrading disease in the subject. The invention further provides a kit or protocol for detecting arthritis or other joint degrading disease by detecting lubricin, the lubricin comprising a joint tissue posttranslational modification.

8 Claims, 8 Drawing Sheets

Figure 1D:
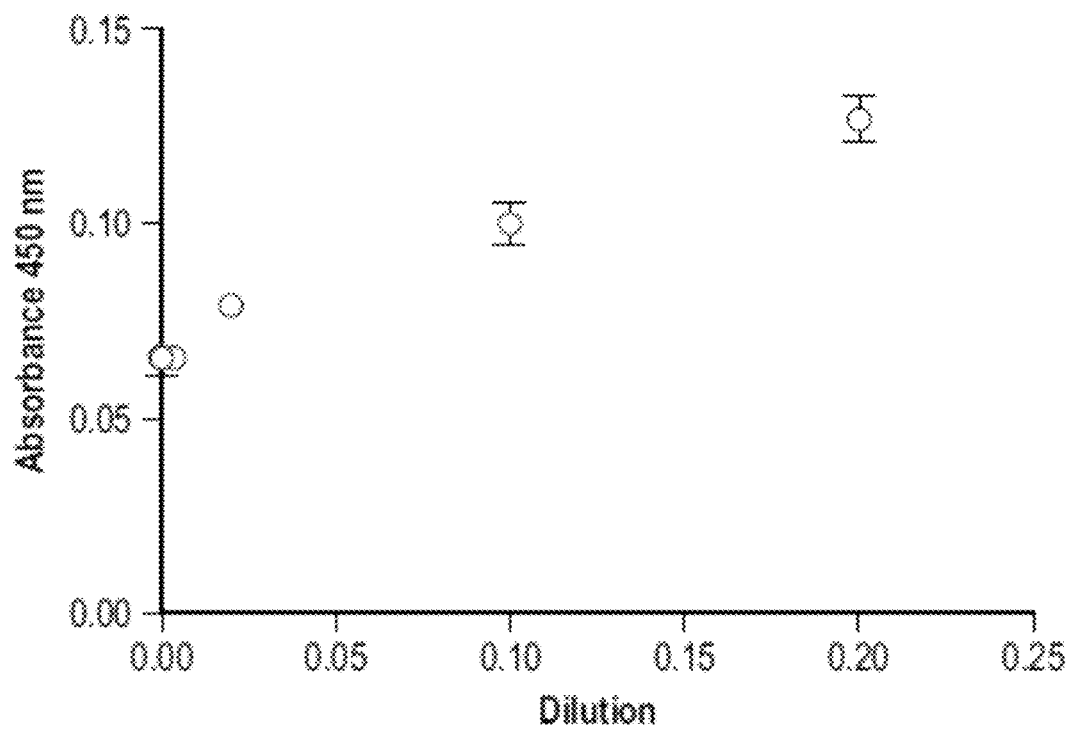

Specification includes a Sequence Listing.

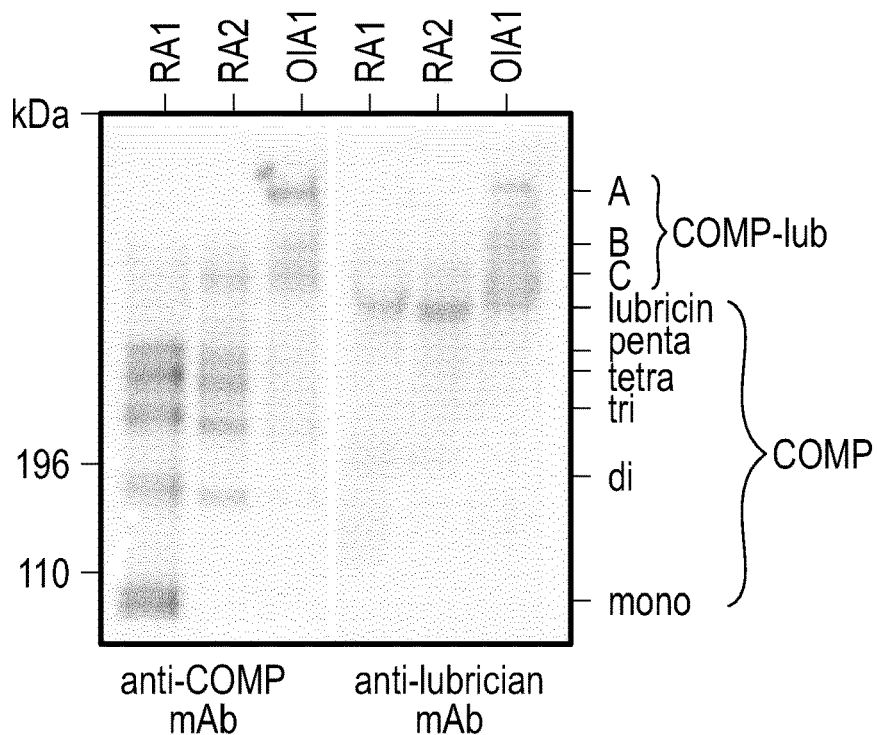
FIG. 1A
| Band | Lubricin | COMP |
|---|---|---|
| A | $1 \times 10^{-816.2}$ (77, 785) | $1 \times 10^{-8.2}$ (2, 2) |
| B | $1 \times 10^{-145.0}$ (15, 24) | $1 \times 10^{-19.2}$ (3, 3) |
| C | $1 \times 10^{-116.7}$ (13, 21) | $1 \times 10^{-163.4}$ (14, 24) |
FIG. 1B
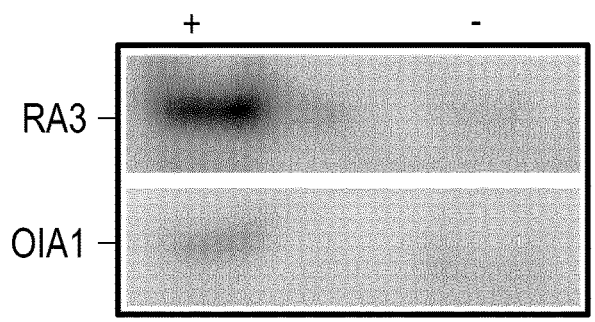
FIG. 1C

SEQUENCE LISTING

<160> NUMBER OF SEQ ID NOS: 15

<210> SEQ ID NO 1
<211> LENGTH: 7
<212> TYPE: PRT
<213> ORGANISM: Homo sapiens

<400> SEQUENCE: 1

Glu Pro Ala Pro Thr Thr Lys
1               5

<210> SEQ ID NO 2
<211> LENGTH: 9
<212> TYPE: PRT
<213> ORGANISM: Homo sapiens

<400> SEQUENCE: 2

Phe Thr Arg Arg Met Thr Pro Thr Pro
1               5

<210> SEQ ID NO 3
<211> LENGTH: 27
<212> TYPE: PRT
<213> ORGANISM: Homo sapiens

<400> SEQUENCE: 3

Cys Thr Ala Glu Leu Ser Cys Lys Gly Arg Cys Phe Glu Ser Phe Glu
1               5                   10                  15

Arg Gly Arg Glu Cys Asp Cys Asp Ala Gln Cys
            20                  25

<210> SEQ ID NO 4
<211> LENGTH: 7
<212> TYPE: PRT
<213> ORGANISM: Homo sapiens

<400> SEQUENCE: 4

Cys Phe Glu Ser Phe Glu Arg
1               5

<210> SEQ ID NO 5
<211> LENGTH: 11
<212> TYPE: PRT
<213> ORGANISM: Homo sapiens

<400> SEQUENCE: 5

Val Cys Thr Ala Glu Leu Ser Cys Lys Gly Arg
1               5                   10

<210> SEQ ID NO 6
<211> LENGTH: 12
<212> TYPE: PRT
<213> ORGANISM: Homo sapiens

<400> SEQUENCE: 6

Gly Asp Ala Cys Asp Asp Asp Ile Asp Gly Asp Arg
1               5                   10

<210> SEQ ID NO 7
<211> LENGTH: 12
<212> TYPE: PRT
<213> ORGANISM: Homo sapiens

<400> SEQUENCE: 7

```
Trp Gly Asp Ala Cys Asp Asn Cys Arg Ser Gln Lys
1               5                   10
```

<210> SEQ ID NO 8
<211> LENGTH: 10
<212> TYPE: PRT
<213> ORGANISM: Homo sapiens

<400> SEQUENCE: 8

```
Arg Val Cys Thr Ala Glu Leu Ser Cys Lys
1               5                   10
```

<210> SEQ ID NO 9
<211> LENGTH: 4
<212> TYPE: PRT
<213> ORGANISM: Homo sapiens

<400> SEQUENCE: 9

```
Asp Asn Cys Arg
1
```

<210> SEQ ID NO 10
<211> LENGTH: 9
<212> TYPE: PRT
<213> ORGANISM: Homo sapiens

<400> SEQUENCE: 10

```
Glu Pro Thr Ser Thr Thr Cys Asp Lys
1               5
```

<210> SEQ ID NO 11
<211> LENGTH: 9
<212> TYPE: PRT
<213> ORGANISM: Homo sapiens

<400> SEQUENCE: 11

```
Cys Ile Asn Thr Ser Pro Gly Phe Arg
1               5
```

<210> SEQ ID NO 12
<211> LENGTH: 26
<212> TYPE: PRT
<213> ORGANISM: Homo sapiens

<400> SEQUENCE: 12

```
Gln Val Cys Thr Asp Ile Asn Glu Cys Glu Thr Gly Gln His Asn Cys
1               5                   10                  15

Val Pro Asn Ser Val Cys Ile Asn Thr Arg
            20                  25
```

<210> SEQ ID NO 13
<211> LENGTH: 11
<212> TYPE: PRT
<213> ORGANISM: Homo sapiens

<400> SEQUENCE: 13

```
Gln Glu Pro Val Gln Lys Cys Pro Gly Arg Arg
1               5                   10
```

<210> SEQ ID NO 14
<211> LENGTH: 4
<212> TYPE: PRT
<213> ORGANISM: Homo sapiens

<400> SEQUENCE: 14

```
Cys Pro Glu Arg
1

<210> SEQ ID NO 15
<211> LENGTH: 21
<212> TYPE: PRT
<213> ORGANISM: Homo sapiens

<400> SEQUENCE: 15

Asp Gly Ser Arg Ser Cys Val Cys Ala Val Gly Trp Ala Gly Asn Gly
1               5                   10                  15

Ile Leu Cys Gly Arg
            20
```

METHOD OF DIAGNOSING ARTHRITIS OR OTHER JOINT DEGRADING DISEASE

CROSS-REFERENCE TO RELATED APPLICATIONS

This application is a Submission under 35 U.S.C. § 371 for U.S. National Stage Patent Application of, and claims priority to, International Application Number PCT/EP2017/054117 entitled METHOD OF DIAGNOSING ARTHRITIS OR OTHER JOINT DEGRADING DISEASE, filed Feb. 23, 2017, which is related to and claims priority to Swedish Patent Number 1650230-4, filed Feb. 23, 2016, the entirety of all of which are incorporated herein by reference.

TECHNICAL FIELD OF THE INVENTION

The present application is filed with a Sequence Listing as a text file, in computer readable form, via EFS-Web. The Sequence Listing is provided as a file entitled 2013-3PUS_Sequence_Listing.txt created on Apr. 28, 2020, which is 2,861 bytes in size. The information in computer readable form is incorporated herein by reference in its entirety.

The present invention relates generally to the field of methods of, and kits useful for, diagnosing arthritis and other joint degrading disease.

BACKGROUND OF THE INVENTION

One main challenge for the public health systems around the world is to adapt to the needs of the aging population. To remain mobile despite aging is an important personal lifestyle attribute that can be directly translated into decreased cost in geriatric care. One major disease impacting on the mobility of an aging application is the type of arthritis known as osteoarthritis.

Osteoarthritis has reached an epidemic disease status in the westernized society. The overall incidence of osteoarthritis is 14% of adults aged 25 and over, and for elderly people (>65 years) it increases to 34%. The outlook for many of the current osteoarthritis patients is bleak. While regenerative medicine and stem cell therapy show promise to restore damaged cartilage by transplantation of cartilage cells, these techniques are still in its infancy and will be expensive. Surgical joint replacement is currently the treatment for end-stage osteoarthritis of the hip and knee. There are currently almost 30 000 hip and knee replacements performed annually only in Sweden, giving an estimated total cost for just the surgery to several billions SEK. In addition, the large number of patients has resulted in an extended waiting list for the surgery.

To limit the cost, wait list and need for surgery, an early stage diagnosis is required. This can halt degradation of cartilage in osteoarthritis by initiating lifestyle changes. One successful treatment for osteoarthritis is the supported osteoarthritis self-management program, Artrosskolan, (www.boaregistret.se). It has shown that if osteoarthritis is diagnosed in an early stage, lifestyle changes, physiotherapy and education can successfully delay or prevent aggravation of the disease and enable management of pain, and prevent loss of function and mobility due to cartilage degradation.

Current diagnostics for osteoarthritis combine patient history with physical examination and imaging techniques such as plain radiographs. Radiographic and physical examinations however only detects established osteoarthritis when macroscopic pathological damage of the tissue already has occurred, at which stage life style changes, physiotherapy and education no longer may be effective in managing the disease.

In addition to research into regenerating damaged joint tissue using stem cell therapy, ongoing research in the field of osteoarthritis further focuses on suppressing the pathological degradation of biomolecules in the joints and maintaining and improving defective lubrication of the joints.

An early diagnosis is also needed for these proposed treatments in order to ensure a successful outcome at a manageable cost to society.

US20070111327A1 discloses a method of detecting lubricin in a sample, such as synovial fluid, by using a first antibody that binds to an amino acid sequence present in lubricin and using a second antibody that binds to a carbohydrate moiety attached to lubricin. Diagnosis of a degenerative joint condition is performed by comparing the amount of lubricin present in the sample, as detected by the method, and comparing it to reference samples. The method appears to only determine the amount of any lubricin present in the sample. Svala E et al., "Characterization of lubricin in synovial fluid from horses with osteoarthritis" discloses that there is a change in glycosylation profile of lubricin in synovial fluid from diseased equine joints compared with normal joints. The method could not be used to detect any disease related changes in glycosylation profile of lubricin in blood due to the relatively high concentration of lubricin not having a change in glycosylation profile in the blood.

Coles J M et al., "Molecular mechanisms of aqueous boundary lubrication by mucinous glycoproteins" is a review of different articles on mucins and lubricin. This review states disulfide bonding of PRG4, i.e. lubricin, to form PRG4 dimers and oligomers was necessary for maintaining low friction. The review further states disulfide bonding was not necessary for wear protection.

OBJECT OF THE INVENTION

In light of the abovementioned need it is a first object of the present invention to provide a method of diagnosing arthritis or other joint degrading disease.

It is a further object of the present invention to provide a method of diagnosing early stage arthritis or joint degrading disease, which is suitable for screening at least a part of a population, which may be susceptible to these types of diseases.

It is yet a further object of the present invention to provide a kit or protocol suitable for diagnosing arthritis or other joint degrading disease.

SUMMARY OF THE INVENTION

At least one of the abovementioned objects, or at least one of further objects which will become evident from the following description, is according to a first aspect of the present invention attained by a method of diagnosing arthritis or other joint degrading disease in a subject which comprises determining whether there is a presence or increase of lubricin, the lubricin having a joint tissue (synovial tissue, cartilage and tendon) posttranslational (pathological or non-pathological) modification, in a blood sample from the subject, the presence or increase indicating arthritis or other joint degrading disease in the subject.

Thus the present invention is based on the hypothesis, which hypothesis has subsequently been validated as shown in the examples and especially FIG. 3B, that specific molecular modification of the lubricating surfaces in joint tissue makes this tissue unique in the body. One way these molecular modifications manifest themselves is by joint tissue posttranslational modification of lubricin molecules. Shedding of the lubricin molecules from the joint surface during joint degradation or other secretion of lubricin directly from joint tissue cells provides a pool of soluble joint tissue modified lubricin i.e. lubricin having a joint tissue "specific" posttranslational modification. This lubricin could leak into inter alia blood where it can be detected specifically due to these modifications (as opposed to lubricin present naturally in blood). The presence or increase of lubricin having a joint tissue posttranslational modification would then indicate an initiation of arthritis or other joint degrading disease.

The present invention further relates to a kit or protocol for detecting arthritis or other joint degrading disease by detecting lubricin, the lubricin having a joint tissue posttranslational modification, the kit or protocol comprising a first agent adapted to detect the joint tissue posttranslational modification (of the lubricin).

Using this kit or protocol it will for the first time be possible to diagnose arthritis and other joint degrading disease in a clinical practice.

BRIEF DESCRIPTION OF THE FIGURES AND DETAILED DESCRIPTION

A more complete understanding of the abovementioned and other features and advantages of the present invention will be apparent from the following detailed description of preferred embodiments in conjunction with the appended drawings, wherein:

FIG. 1 shows lubricin having a joint tissue specific posttranslational modification, the modification comprising the covalent binding of COMP to the lubricin in the synovial fluid of arthritis patients, FIG. 2 shows methods for transferring glycoprotein biomarker discovery from research to clinic, FIG. 3 shows pathological joint tissue modifications to lubricin, which pathological modification are potential candidates to be detected in plasma, FIG. 4 shows that lubricin tightly adheres to cartilage matrix proteins suggesting that the shedding of lubricin from the joint surface will bring these matrix proteins into the synovial fluid and further transported into plasma, and FIG. 5 shows that lubricin can associate to matrix proteins via disulfide bonds, making it a joint tissue modification of lubricin.

The first aspect of the present invention relates to a method of diagnosing arthritis or other joint degrading disease in a subject which method comprises determining whether there is a presence or increase of lubricin having a joint tissue posttranslational modification, in a blood sample from the subject, the presence or increase of said lubricin having said joint tissue posttranslational modification indicating arthritis or other joint degrading disease in the subject.

Figure 3A:
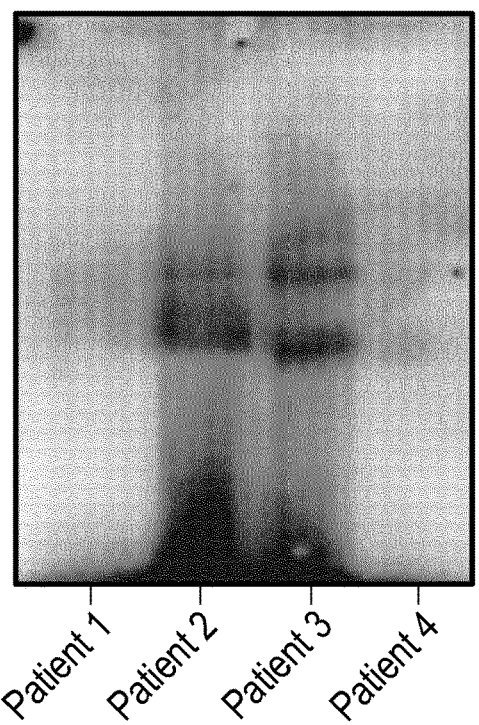
Figure 3B:
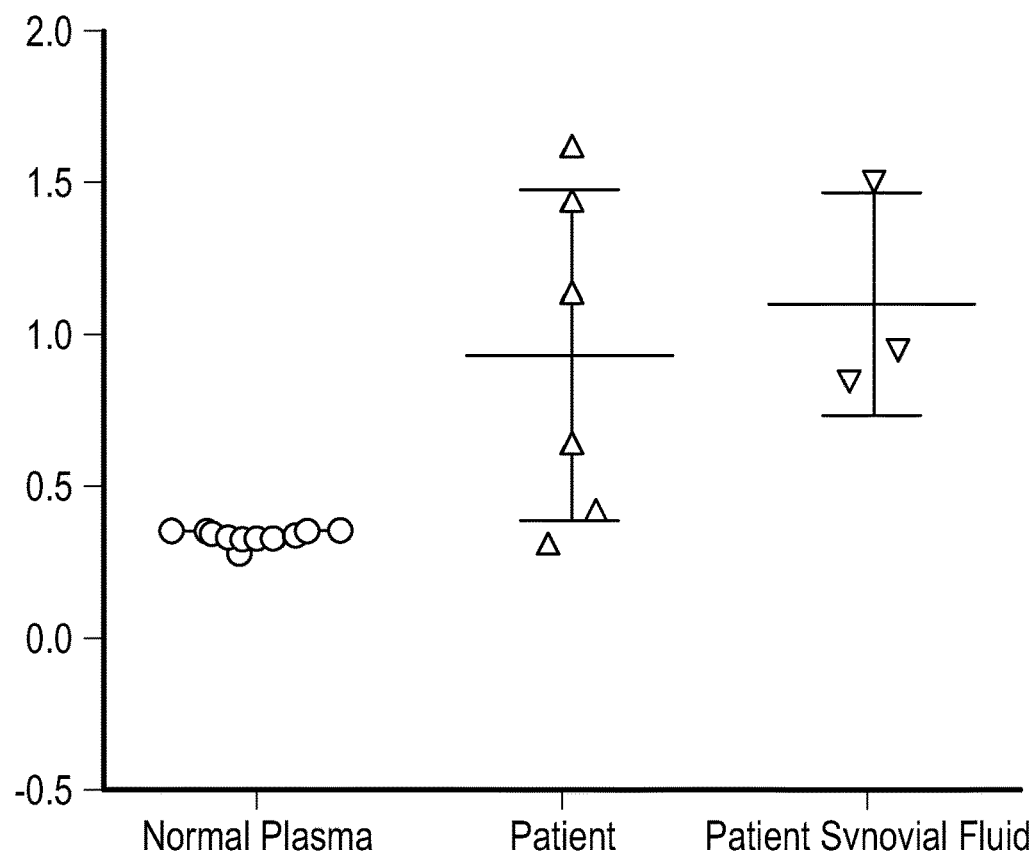

As discussed above and as shown in the examples and especially FIG. 3B, arthritis and other joint degrading disease manifest themselves by shedding off or changing the production of lubricin, which lubricin has joint tissue posttranslational modifications, from the joint surfaces, which lubricin is then leaked into inter alia blood where it can be detected.

By the method according to first aspect of the present invention this lubricin, having the joint tissue posttranslational modification, is detected thereby providing a diagnosis of arthritis or other joint degrading disease sufficiently early to allow patients to be directed into the lifestyle changes needed or other therapy to prevent chronic joint damage such as chronic knee damage.

In the healthy state the surfaces of joint tissue are the ultimate lubricating system with nearly zero friction even at high load. Chondrocytes (embedded in the cartilage) and synovial fibroblast (in the synovial membranes) are secreting proteins into the lubricating synovial fluid in the area between joints. Proteins from the synovial fluid are recruited to the joint surfaces efficiently, specifically to form the superficial layer of lubrication. Proteins are also produced directly from the chondrocyte to contribute to the superficial layer. This layer in the superficial zone on cartilage consists predominantly of the carbohydrate rich glycoprotein, lubricin, which provides this essential lubrication and protection in a healthy state.

There have previously been reported indications that these carbohydrates and the assembly of this layer is altered in arthritic diseases due to defect in synoviocytes, synovial fibroblast and/or chondrocyte biosynthesis (both quality and quantity) as well as a defect localization of lubricin to the joint surface. However, the present inventors have here for the first time shown that molecular joint tissue modification, and alteration of these modifications, found on lubricin correlate with osteoarthritis associated degradation in a disease state, and that lubricin having joint tissue specific posttranslational modifications, i.e. lubricin comprising these molecular alternations, are detectable in easily obtainable samples and furthermore can be used in clinical practice by being detectable using techniques familiar to clinical laboratories.

As samples from healthy subjects normally may contain free or native lubricin it should be emphasized that it is only the presence, increase, or absence of lubricin having a joint tissue posttranslational modification which is to be determined.

Blood samples in particular contain high concentrations of lubricin not having a joint tissue posttranslational modification. Accordingly, it is not enough to merely detect lubricin in a blood sample, it must further be ascertained that the detected lubricin carries or has a joint tissue posttranslational modification in order to conclude that the lubricin has indeed been shed from the joint and to therefrom diagnose osteoarthritis or other joint degrading disease.

The method of diagnosing osteoarthritis according to the first aspect of the present invention is performed in vitro on a blood sample taken from the subject.

The subject is preferably a mammal, and most preferably a human.

A human subject may be male or female. The human subject may be suspected or tentatively diagnosed with arthritis. The human subject may suffer from pain in, or swelling of, one or more joints.

Where the subject is not a human the subject is preferably a dog or a horse, or other valuable animal.

In the context of the present invention arthritis is to be understood as encompassing degenerative arthritis, degenerative joint disease, or osteoarthrosis.

Preferably the arthritis is osteoarthritis.

The arthritis may, for a human subject, for example affect the joints near the ends of the fingers, at the base of the thumb, at the neck, the lower back, the knees, and the hips of a human subject.

The arthritis may be caused by joint injury, abnormal joint or limb development, or inherited factors.

In the context of the present invention determining is to be understood as encompassing detecting, measuring, quantifying, qualifying, and/or classifying.

The presence, and conversely the absence, of the lubricin having a joint tissue posttranslational modification may be determined either directly, i.e. by determining whether there are joint tissue derived lubricin molecules in the sample, or indirectly by probing the sample using a probe designed to indicate the presence of an entity associated with lubricin having a joint tissue posttranslational modification.

In any case it must be ascertained that the lubricin indeed carries or has a joint tissue posttranslational modification.

The increase of lubricin having a joint tissue posttranslational modification may be determined by comparing the concentration of the lubricin in the sample with the concentration of the lubricin in an earlier sample from the same subject, or by comparing the concentration of the lubricin in the sample with the concentration of the lubricin in a sample from a healthy subject, i.e. a subject known to not suffer from arthritis or other joint degrading disease.

The term "joint tissue posttranslational modification" means that the entity referred to, i.e. lubricin, has been modified posttranslationally in a way from which it can be concluded that it is derived from a joint tissue area.

Thus the joint tissue posttranslational modification may be a modification present in lubricin involved in the normal (disease free) operation of a joint. Alternatively the synovial specific posttranslational modification may be a modification which is up-regulated during, or as a result of, the disease process.

This indicates that lubricin so modified, when its presence or increase is determined in the sample in the sample, has been shed or leaked from the joint tissue, e.g. shed from the joint surfaces, thus indicating arthritis or other joint degrading disease in the subject.

The joint tissue posttranslational modification may be a glycosylation (carbohydrates attached to lubricin), a folding (how the lubricin protein is folded into the 3D structure) disulfide bridges, proteolytic degradation and/or a covalent/non-covalent complexation (lubricin forms complexes with one or more further proteins).

In the context of the present invention indicating is to be understood as encompassing one or more of ascertaining, determining, implying, proving, evidencing and symbolizing. Thus in one embodiment the presence or increase of lubricin having a joint tissue posttranslational modification in the sample may evidence arthritis, such as osteoarthritis, or other joint degrading disease, while in another embodiment the presence or increase may merely imply osteoarthritis or other joint degrading disease. The concentration of the lubricin having a synovial specific posttranslational modification, and the nature, such as the extent, of the joint tissue posttranslational modification, in the sample will vary depending on the severity of these diseases, thus the indication of the diseases will vary in strength from implying to proving. Further, the determining of the presence of lubricin with different types of joint tissue posttranslational modifications will carry different weight in indicating osteoarthritis. One example of different types of joint tissue posttranslational modifications is the extent of glycan epitopes and the extent of sialic acid on the lubricin.

The lubricin may have more than one joint tissue posttranslational modification, and the determining of the presence of the lubricin may comprise determining the presence of more than one joint tissue posttranslational modification on the lubricin.

Also the alteration of the extent and nature of the joint tissue posttranslational modification between one sample and another sample may be determined.

In the preferred embodiment of the method according to the first aspect of the present invention the sample is a blood sample, however it is contemplated within the context of the present invention that the sample could be selected from the group consisting of synovial fluid, urine, saliva, and tissue.

All of these possible alternatives represent more or less easily obtainable samples.

Blood sample encompasses whole blood as well as one or more individual components of whole blood.

In the preferred embodiment of the method according to the first aspect of the present invention the blood sample is selected from the group consisting of serum and plasma.

Serum and plasma are readily obtainable samples and are used in general clinical practice as samples for diagnosis of other diseases. Thus these samples are suitable for screening for arthritis and other joint degrading disease among the general population.

It is further contemplated within the context of the present invention that a sample selected from the group consisting of cartilage, synovial membrane and synovial tissue could be used instead of a blood sample.

These samples are less readily available, and thus less suited for screening, however they may still be advantageous and may for example be obtained whenever access to a joint, typically by surgery, is provided for other reasons. Further this type of sample may be used to confirm an initial diagnosis, for example obtained using serum or plasma as the sample, where the initial diagnosis is such as to warrant obtaining a tissue sample. This may be the case where the presence of lubricin having a joint tissue posttranslational modification in the serum or plasma sample merely implies arthritis or joint degrading diseases.

In the preferred embodiment of the method according to the first aspect of the invention the method comprises discriminating between lubricin having the joint tissue posttranslational modification, and lubricin not having the joint tissue posttranslational modification, in the blood sample, whereby only the presence or increase of the lubricin having the joint tissue posttranslational modification indicates arthritis or other joint degrading disease in the subject.

This is important because a blood sample naturally contains large amounts of lubricin, which does not have or carry a posttranslational modification identical to the one produced in the joint tissue. The amount or concentration of lubricin having the joint tissue posttranslational modification in the blood sample may be several magnitudes smaller than the amount or concentration of lubricin not having the joint tissue posttranslational modification.

In the preferred embodiment of the method according to the first aspect of the invention the method comprises determining the presence or increase of lubricin having the joint tissue posttranslational modification, and the method further comprises not determining the presence or increase of lubricin not having the joint tissue posttranslational modification.

As above it is important to only determine the presence or increase of lubricin having the joint tissue posttranslational modification as it is only this lubricin that can indicate arthritis or other joint degrading disease in the subject.

In the preferred embodiments of the method according to the first aspect of the present invention the joint tissue posttranslational modification is selected from the group consisting of the binding of carbohydrates to the lubricin (i.e. carbohydrates are attached to the lubricin) and/or the binding of a further (other) joint tissue protein to the lubricin and/or proteolytic cleavage. Proteolytic cleavage refers to proteolytic cleavage of the lubricin such as a proteolytic cleavage that is specific for lubricin in joint tissue.

The binding of carbohydrates to lubricin is also known as glycosylation. The binding of a further joint tissue protein to lubricin results in a complex. The binding may be covalent or non-covalent. The binding may be a disulfide bound provided by cysteines in lubricin to the further joint tissue protein.

The further joint tissue protein may also be called lubricin binding partner.

In the preferred embodiments of the method according to the first aspect of the present invention the further joint tissue protein is selected from the group consisting of, preferably mammalian versions of, Cartilage Oligomeric Matric Protein (COMP), fibronectin, and collagen type II, or parts thereof.

COMP, fibronectin and collagen type II are known to the person skilled in the art and description of these proteins can be found in international protein databases such as uniprot (www.uniprot.org).

These further joint tissue proteins are all involved in the proper functioning of a joint, and are interacting with lubricin on the joint surface. Accordingly the presence of a complex between any of these proteins and lubricin indicates that the detected complexes, which include a part of the complexes in the joint, have been involved in maintaining the functioning of the joint, but these complexes are now shed from the joint and thereby indicate a degeneration of the proper functioning of the joint.

In the preferred embodiments of the method according to the first aspect of the present invention the further synovial protein is Cartilage Oligomeric Matrix Protein or parts thereof.

As stated above the COMP is important in the proper functioning of the joint. Accordingly the determination of the presence of such a complex in the sample is a strong indication of arthritis.

In the preferred embodiments of the method according to the first aspect of the present invention the presence or increase of the lubricin having the joint tissue posttranslational modification is detected using a method selected from the group consisting of ELISA or sandwich ELISA, Proximity Ligation Assay, Proximity Extension Assay, and/or Mass Spectrometry.

Of these ELISA is generally easiest to implement in the clinic.

In the preferred embodiments of the method according to the first aspect of the present invention the presence or increase of the lubricin having the joint tissue posttranslational modification is detected using ELISA with a first agent adapted to bind to the joint tissue posttranslational modification and a second agent adapted to bind to the lubricin.

This ensures that only lubricin having the joint tissue posttranslational modification is detected.

In the preferred embodiments of the method according to the first aspect of the present invention the method further comprises determining the extent of the joint tissue posttranslational modification.

This is advantageous as the extent of the joint tissue posttranslational modification provides may be used to diagnose the stage of the arthritis or joint degrading disease.

The extent of the joint tissue posttranslational modification may for example be determined using Mass Spectrometry whereby a more highly modified lubricin, e.g. lubricin or parts thereof forming a complex with a plurality of further joint tissue proteins (or parts thereof), is detected with a higher mass than can be expected without this modification. In the case of glycosylation, the detection of joint tissue lubricin or parts thereof will manifest as an altered mass or molecular entity present on lubricin protein backbone (or parts thereof) compared to non-joint tissue derived lubricin.

The present invention further relates to a kit or protocol for detecting arthritis or other joint degrading disease by detecting lubricin, the lubricin having a joint tissue posttranslational modification, the kit or protocol comprising a first agent adapted to detect the joint tissue posttranslational modification.

Using this kit it will for the first time be possible to diagnose arthritis and other joint degrading disease in a clinical practice.

In the context of the present invention "detect" is to be understood as encompassing binding to and/or interact with, the requirement being that the first agent interacts with/binds to the joint tissue posttranslational modification so that the presence of the lubricin having the joint tissue posttranslational modification is determined.

The first agent may detect the synovial specific posttranslational modification directly, by providing some visually discernable change (i.e. color, formation of a gas, etc.) or by providing the possibility of detecting the synovial specific posttranslational modification in a subsequent process such as Mass Spectrometry with or without prefractionation of the sample.

In the preferred embodiment of the kit or protocol according to the second aspect of the present invention the kit or protocol further comprises a second agent adapted to detect the lubricin by binding to the lubricin or parts thereof, the first agent being adapted to bind to carbohydrates bound to the lubricin or a further joint tissue protein (or parts thereof) bound to the protein.

The first agent (also known as a joint tissue posttranslational modification agent) is preferably an antibody in the case where the modification is a further joint tissue protein, or a carbohydrate binding molecule such as an antibody or lectin in the case that the joint tissue posttranslational modification is a carbohydrate.

One of the first and second agents may be attached to a support so as to immobilize the lubricin whereby the other one of the first and second agents may carry a probe molecule such as a fluorescent or luminescent molecule, a magnetic particle or radioactive isotope, or an enzyme capable of producing a colorant or a acid, base or gas, when provided with a suitable substrate.

The invention will now be further described with reference to examples 1-5.

EXAMPLE 1

Complexes Between COMP and Lubricin in Synovial Fluid of Arthritis Patients

COMP, Cartilage Oligomeric Matrix Protein, is found in joints and forms complexes with lubricin. FIG. 1 shows complexes between COMP and lubricin in the synovial fluid of arthritis patients. FIG. 1A shows Western blots comparing enriched glycoproteins from arthritis patients' synovial fluid (SF). One Oligomeric Arthritis patient O1A1) and two rheumatoid arthritis (RA1 and RA2) patient samples were separated by SDS-AgPAGE, non-reducing conditions. Lubricin was detected by mAb13; COMP detected by mAb HC484D1. FIG. 1B shows MS identification of proteins from the three high MW bands from O1A1. The statistical confidence of identification from the proteomic search engine X!Tandem (www.thegpm.org) shown for lubricin and COMP for each band as expectation value, or, the probability the identification is a random assignment, hence, the smaller the expectation value, the greater the confidence. In brackets, the numbers of unique and total peptides used in the identification. FIG. 1C shows Co-IP of synovial COMP-lubricin complex from the acidic fraction of SF from patients RA3 and O1A1 (+). mAb HC484D1 COMP was used, with protein G beads, to pull out the COMP-lubricin complex. After SDS-PAGE, a Western blot was used with mAb13 (anti-lubricin) to identify the complex. A no antibody control (−) shows the complex enriched above non-specific binding. FIG. 1D shows Sandwich ELISA of serial dilutions of acidic SF glycoproteins from patient RA4. mAb HC484D1 was used as the capture antibody and the level of tethered lubricin was detected by mAb13 and HRP conjugated rabbit anti-mouse antibody.

In summary of the above example 1 and FIG. 1 show that complexes between COMP and lubricin are present in the synovial fluid of arthritis patients. As COMP is shed from the joint surfaces these complexes will find their way into plasma where they can be detected.

EXAMPLE 2

Figure 2A:
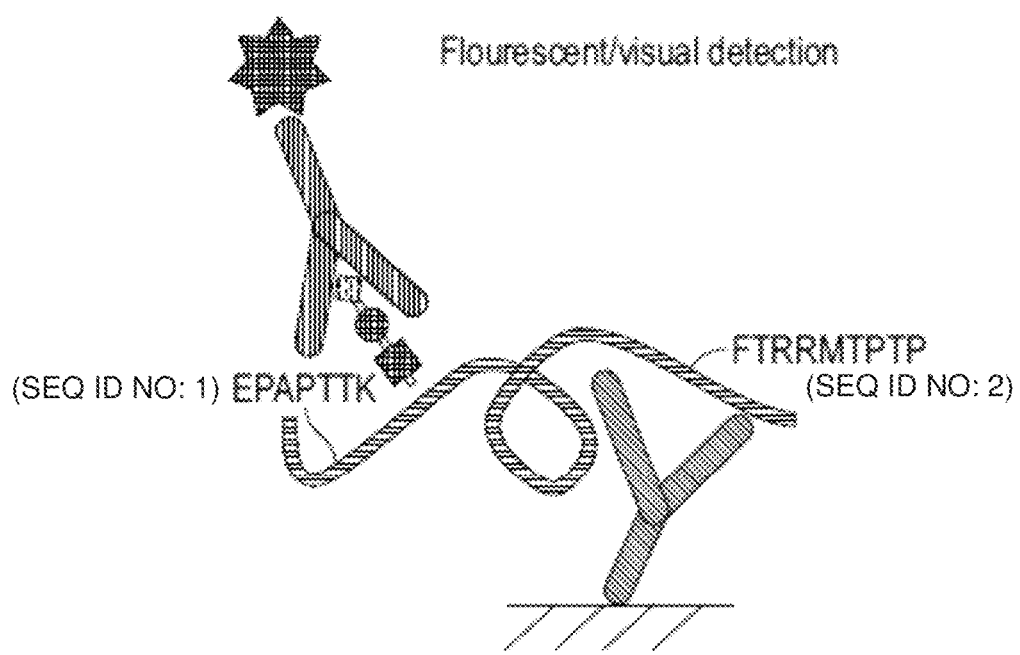
Figure 2B:
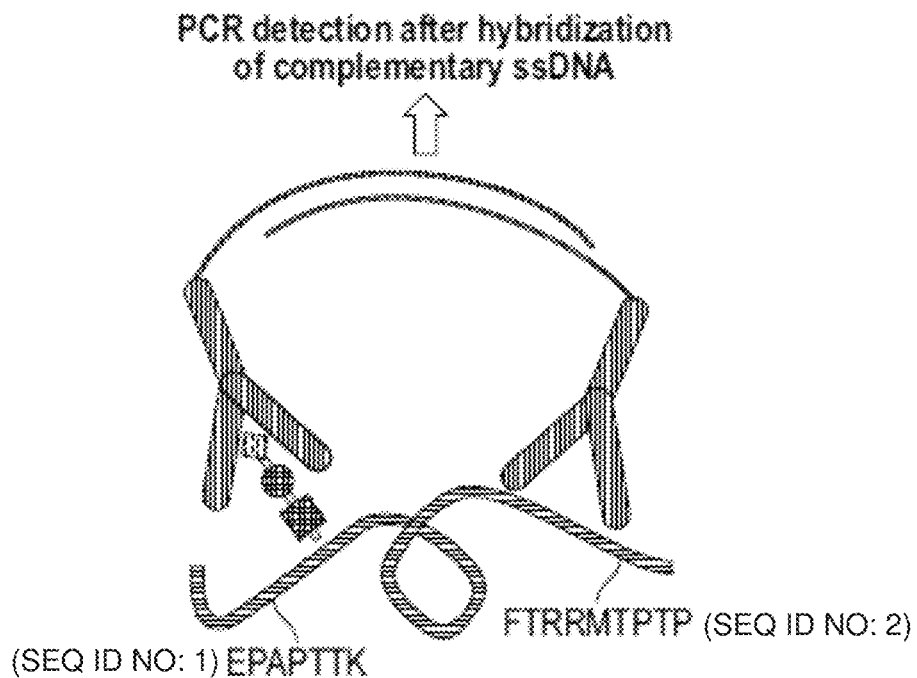
Figure 2C:
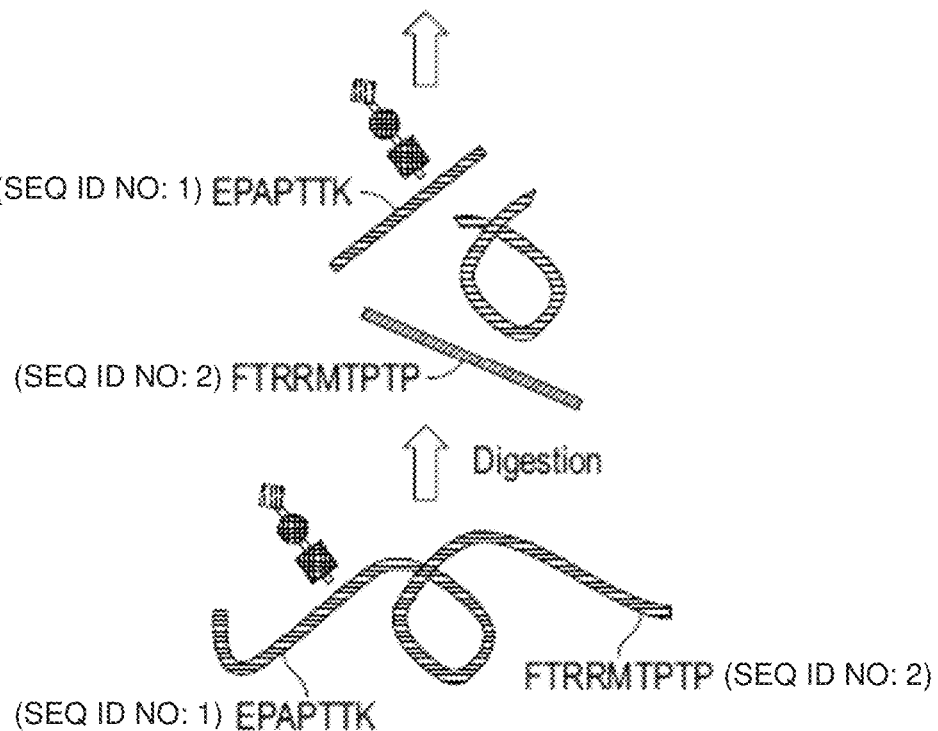

Methods for Transferring Glycoprotein Biomarker Discovery from Research to Clinic FIG. 2 shows different methods for transferring lubricin biomarker discovery from research to clinic. FIGS. 2A and 2B show ELISA and Proximity ligation assay (PLA), respectively, which methods involve utilizing a first antibody against the disease related glycan epitope attached to the lubricin protein core (exemplified by the glycan near the sequence EPAPTTK (SEQ ID NO. 1) known to be glycosylated) and a second antibody against an unmodified area of lubricin (exemplified by the sequence FTRRMTPTP (SEQ ID NO. 2), known to not be glycosylated). FIG. 2C shows mass spectrometry involving monitoring a modified peptide from a unique sequence with a disease related glycan or other attached modification (e.g. peptide from binding protein partner). Alternatively catching antibodies can be used against lubricin protein core to capture lubricin or protein binding partner followed by identifying the type of modification present. For protein binding partner this could be done after proteolytic cleavage followed by mass spectrometric identification/quantification. For glycosylation analysis this could be done after chemical or enzymatical release of oligosaccharide or proteolytic generation of glycopeptides followed by monitoring of the glycoconjugates (e.g. mass spectrometry). It will be evident to one skilled in the art that the roles may be reversed so that it is the modification that is captured and the detection is performed by binding to the lubricin core protein or parts thereof.

Thus example 2 and FIG. 2 show that the method of diagnosis according to the first aspect of the present invention can be used in the clinic.

EXAMPLE 3

Pathological Modifications to Lubricin, which Pathological Modifications are Potential Candidates to be Detected in Plasma FIG. 3 shows pathological modifications to lubricin, which modifications are potential candidates to be detected in plasma. FIG. 3A shows a typical SDS-PAGE pattern of arthritis patient's synovial lubricin on various degrees binding to recombinant L-selectin (probe for sulfated oligosaccharides present on lubricin). Lubricin is detected as monomers and dimers>350 kDa, as polydisperse bands due to the heterogeneous glycosylation (more than 50% of the mass of lubricin). The leakage of joint tissue lubricin into plasma, as shown in FIG. 3B, provides a proof of concept that lubricin having a joint tissue posttranslational modification such as lubricin-COMP complexes can be found in both patients' plasma and synovial fluid. Accordingly, the complexes, which as seen from example 1 and FIG. 1, are associated with arthritis, can be detected in plasma, thus opening up for an effective and simple method of diagnosis for arthritis and joint degrading disease. The experiment was performed using a sandwich-ELISA with α-COMP as catching and α-lubricin for detecting.

EXAMPLE 4

Lubricin Adheres to Various Cartilage Matrix Proteins

Figure 4A:
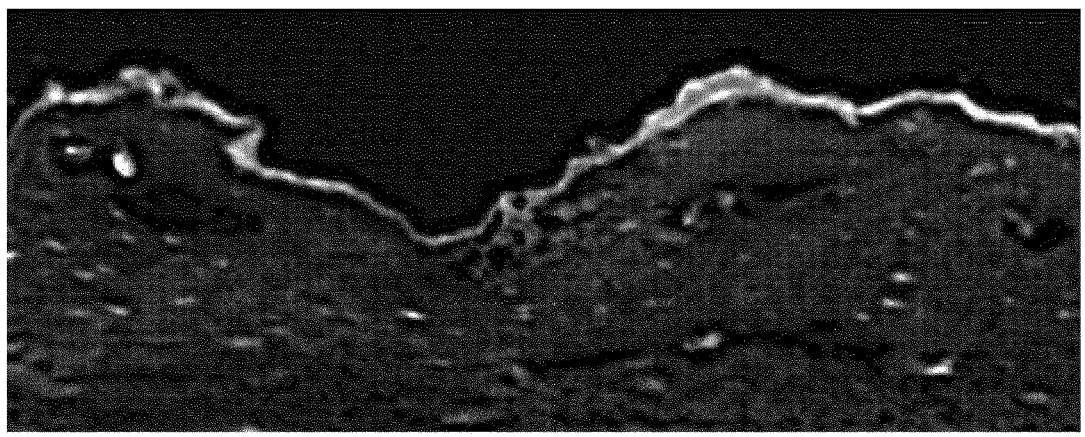
Figure 4B:
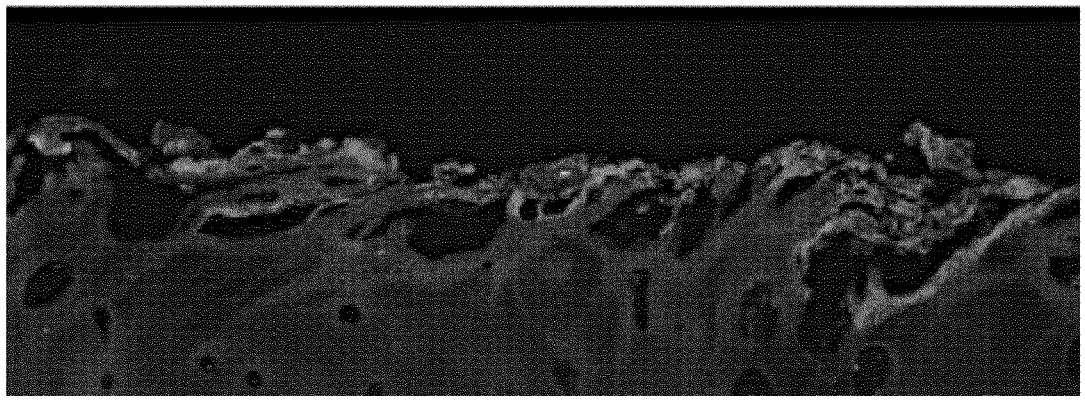
Figure 4C:
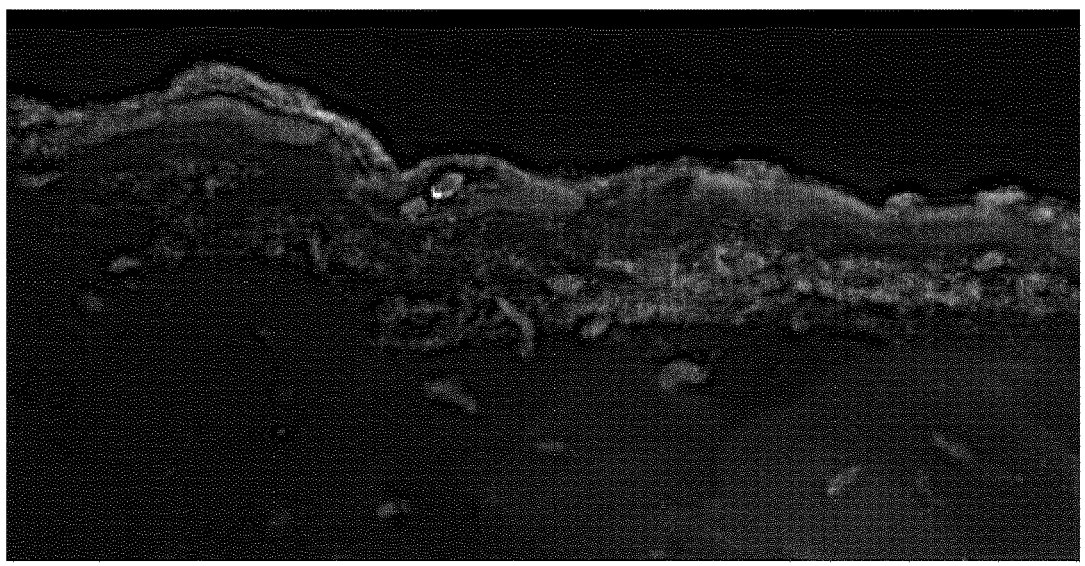

FIGS. 4A-C show that lubricin adheres to cartilage proteins. With lubricin containing unglycosylated parts and glycosylated areas, it has the ability to interact by both protein-protein interactions and carbohydrate-protein interaction with compounds on the cartilage surfaces. These complexes are shed from the cartilage during arthritic degradation into the synovial fluid and further leaked into plasma as shown by example 3 to be detected as biomarker for an initial degradation and diagnosis for early stage arthritis degradation. Thus FIG. 4A shows lubricin binding to fibronectin. FIG. 4B shows lubricin binding to collagen type II, and FIG. 4C shows lubricin binding to cartilage oligomeric matrix protein (COMP).

Accordingly the detection of any of the complexes (containing lubricin with associated proteins or parts thereof) shown in FIGS. 4A-4C is an indication of arthritic degradation.

EXAMPLE 5

Lubricin can Associate to Matrix Proteins Via Disulfide Bonds

FIG. 5 shows that lubricin can associate to matrix proteins via disulfide bonds.

Figure 5A:
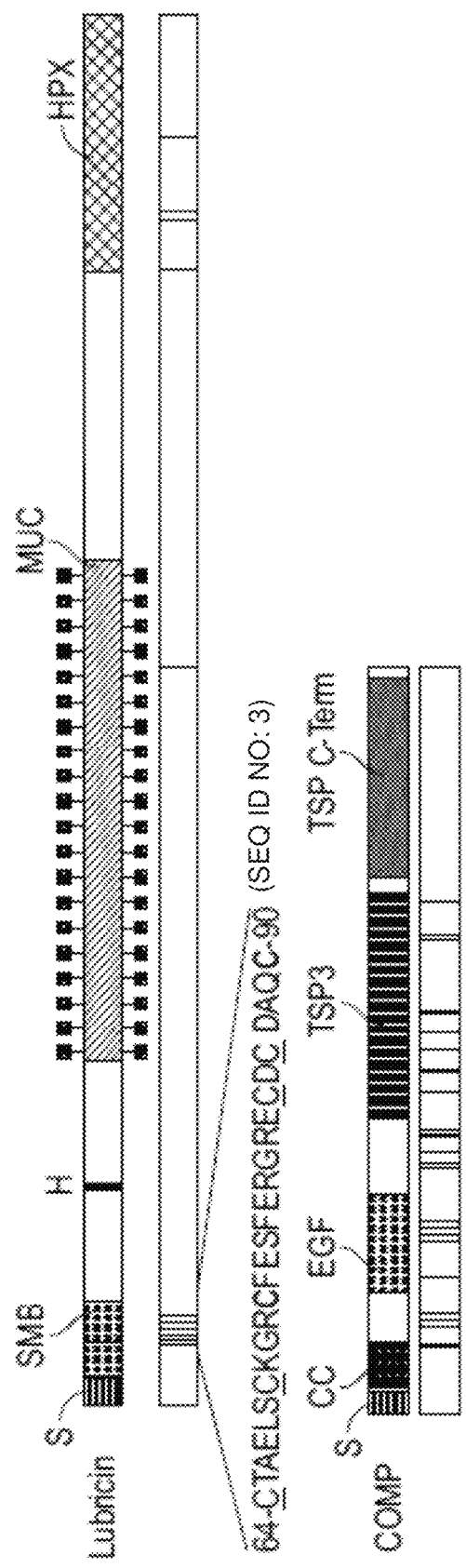

FIG. 5A shows the location of cysteines involved in disulfide bonds with the matrix protein COMP and lubricin. Domain structures shown for COMP and lubricin. Lubricin's signal peptide (S), 2× somatomedin-B domains (SMB), heparin binding domain (H), mucin domain (MUC), hemopexin repeats (HPX). COMP's signal peptide (S), coiled coil domain (CC), 2×EGF Ca-binding domains (EGF), TSP type 3 repeats (TSP 3), TSP C-terminal domain (TSP C-Term). Black lines: cysteines involved in disulfide bonds. The lubricin sequence between amino acids 64 and 90 shown, underlined: cysteines involved in inter-protein disulfide bonds, bold: free cysteines.

Figure 5B:
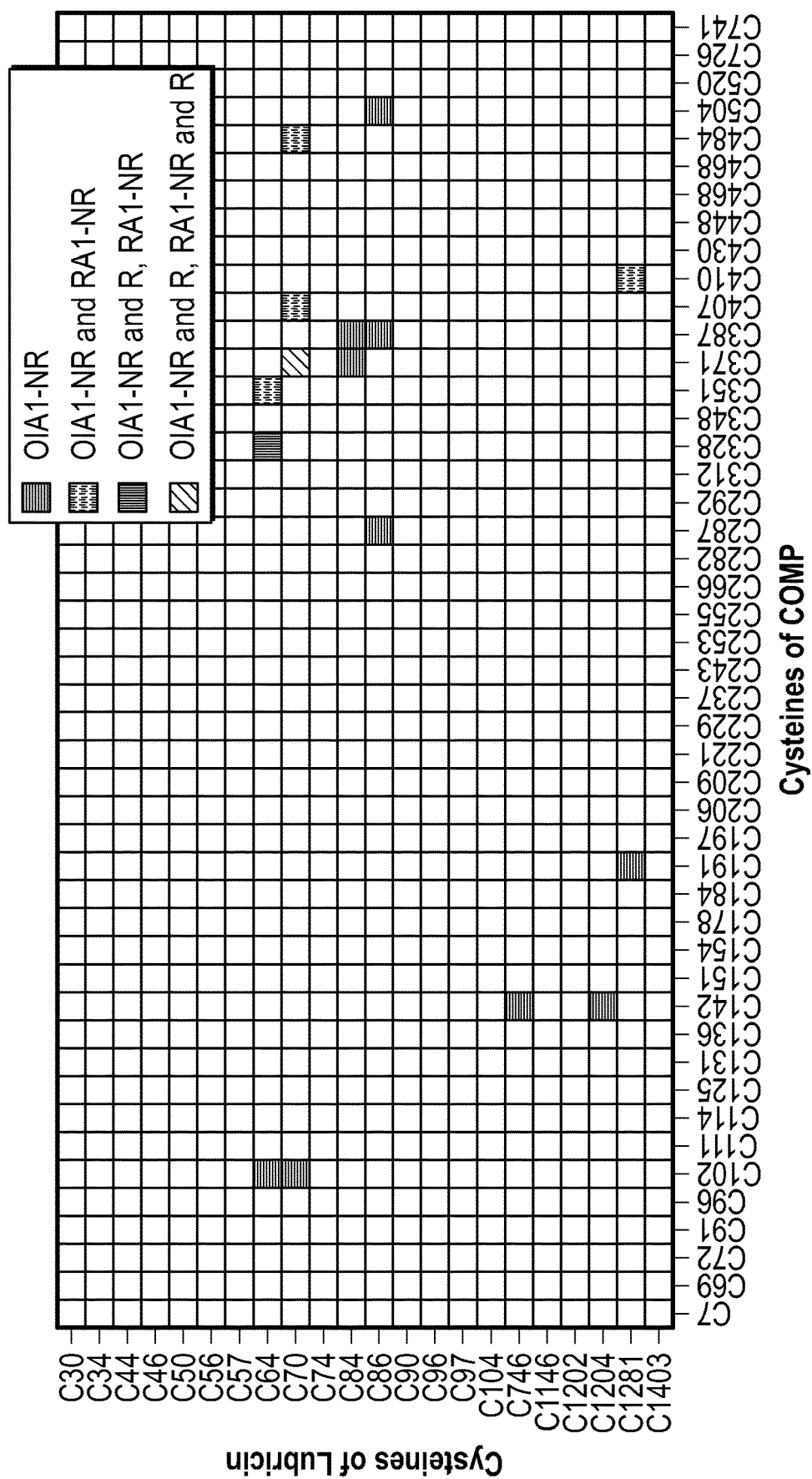

FIG. 5B shows disulfide bonds detected in lubricin. Cysteines of lubricin are shown on y-axis and COMP on x-axis, bonds between them by a grey square. Boxes show where COMP and lubricin were found attached via intra-molecular bonds.

Figure 5C:
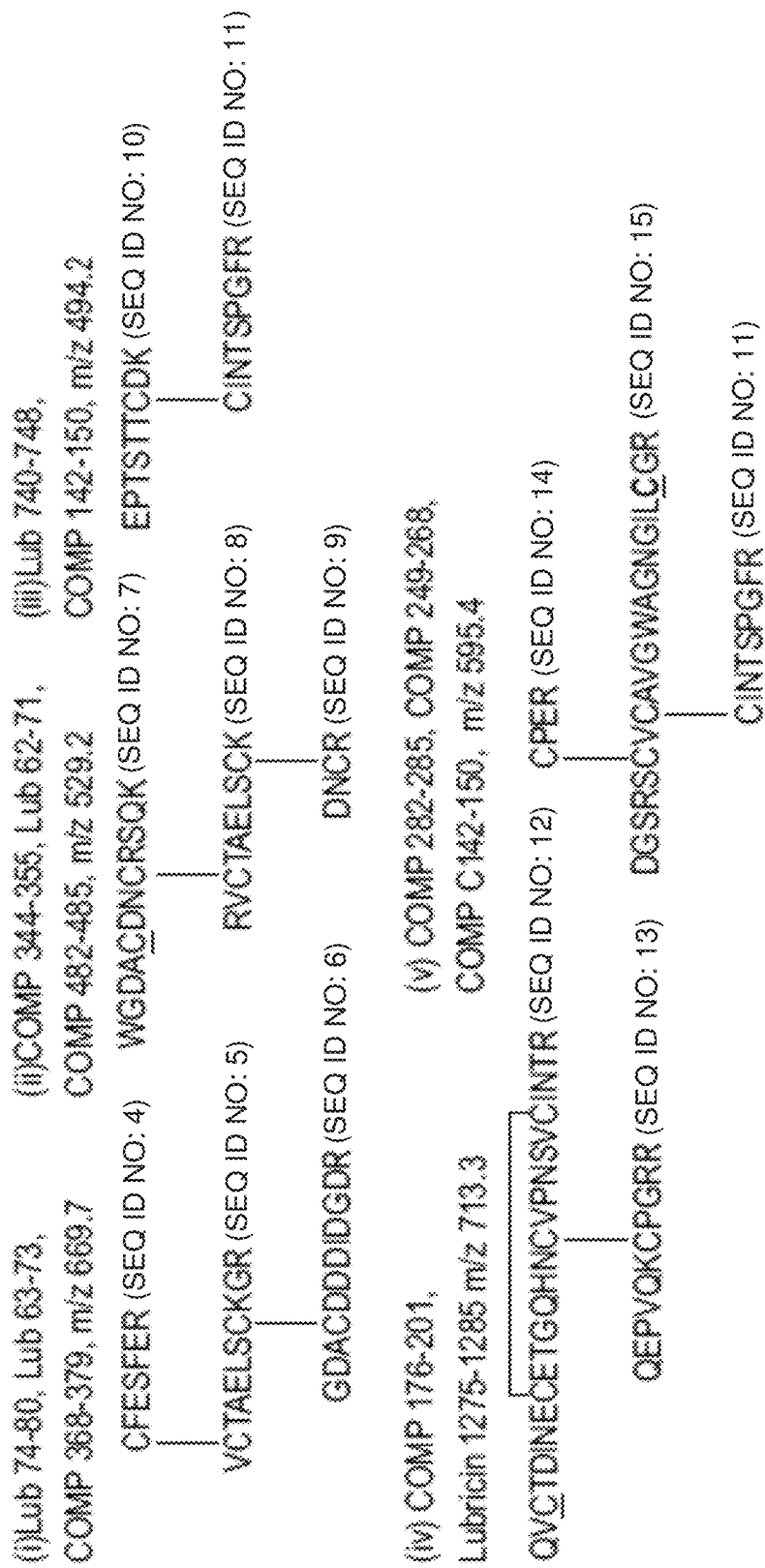

FIG. 5C shows examples of the peptides bound by disulfide bonds including di- and tri-peptide complexes. The peptides' amino acid range is shown above the bound peptides along with the m/z. Bonds are shown by black lines. Underlined C are alkylated cysteines. Bold C are free cysteines, showing that lubricin is a reactive molecule that are capable of forming covalent complexes with matrix protein on the cartilage surface.

The invention claimed is:

1. A method of diagnosing osteoarthritis in a subject, which method comprises:
   detecting an increase of lubricin having a joint tissue posttranslational modification, in a blood sample from said subject;
   diagnosing osteoarthritis in said subject when there is an increase of said lubricin having said joint tissue posttranslational modification; and
   wherein said increase of lubricin having said joint tissue posttranslational modification is detected by comparing the concentration of said lubricin in said sample with the concentration of said lubricin in an earlier sample from the same subject, or by comparing the concentration of said lubricin in said sample with the concentration of said lubricin in a sample from a subject known to not suffer from osteoarthritis,
   wherein said subject is a human suspected of having osteoarthritis, and
   wherein said joint tissue posttranslational modification is selected from the group consisting of the binding of carbohydrates to said lubricin and the binding of a further joint tissue protein to said lubricin, and wherein said further joint tissue protein is selected from the group consisting of Cartilage Oligomeric Matrix Protein, fibronectin, and collagen type II; and
   treating said subject for osteoarthritis with at least one from the group consisting of physiotherapy, lifestyle changes, and stem cell therapy.

2. The method according to claim 1, said blood sample being selected from at least one of the group consisting of serum and plasma.

3. The method according to claim 1, further comprising discriminating between lubricin having said joint tissue posttranslational modification, and lubricin not having said joint tissue posttranslational modification, in said blood sample, whereby only said increase of said lubricin having said joint tissue posttranslational modification indicates arthritis in said subject.

4. The method according to claim 1, wherein said presence of said lubricin having said joint tissue posttranslational modification being detected using a method selected from the group consisting of ELISA or sandwich ELISA, Proximity Ligation assay, Proximity Extension Assay and Mass Spectrometry.

5. The method according to claim 4, wherein said presence of said lubricin having said joint tissue posttranslational modification being detected using ELISA with a first agent adapted to bind to said joint tissue posttranslational modification and a second agent adapted to bind to said lubricin.

6. The method according to claim 1, further comprising detecting the extent of said joint tissue posttranslational modification.

7. A method of treating osteoarthritis in a subject, which method comprises:
   detecting an increase of lubricin having a joint tissue posttranslational modification, in a blood sample from said subject,
   finding an increase of said lubricin having said joint tissue posttranslational modification, and
   wherein said increase of lubricin having said joint tissue posttranslational modification is detected by comparing the concentration of said lubricin in said sample with the concentration of said lubricin in an earlier sample from the same subject, or by comparing the concentration of said lubricin in said sample with the concentration of said lubricin in a sample from a subject known to not suffer from osteoarthritis,
   wherein said subject is a human suspected of having osteoarthritis, and
   wherein said joint tissue posttranslational modification is selected from the group consisting of the binding of carbohydrates to said lubricin and the binding of a further joint tissue protein to said lubricin, and wherein said further joint tissue protein is selected from the group consisting of Cartilage Oligomeric Matrix Protein, fibronectin, and collagen type II,
   treating said subject for osteoarthritis with at least one from the group consisting of physiotherapy and stem cell therapy.

8. The method according to claim 7, wherein said treating of said subject for osteoarthritis comprises regenerating damaged joint tissue using stem cell therapy.

* * * * *